(12) United States Patent
Lu et al.

(10) Patent No.: US 10,531,815 B2
(45) Date of Patent: Jan. 14, 2020

(54) USER-STEERED ON-THE-FLY PATH PLANNING

(75) Inventors: Kongkuo Lu, Sugar Land, TX (US); Rafael Wiemker, Kisdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 660 days.

(21) Appl. No.: 14/115,709

(22) PCT Filed: May 4, 2012

(86) PCT No.: PCT/IB2012/052241
§ 371 (c)(1),
(2), (4) Date: Nov. 5, 2013

(87) PCT Pub. No.: WO2012/153249
PCT Pub. Date: Nov. 15, 2012

(65) Prior Publication Data
US 2014/0081129 A1    Mar. 20, 2014

Related U.S. Application Data

(60) Provisional application No. 61/484,479, filed on May 10, 2011.

(51) Int. Cl.
*A61B 5/06* (2006.01)
*A61B 1/00* (2006.01)
(Continued)

(52) U.S. Cl.
CPC ............ *A61B 5/066* (2013.01); *A61B 1/0002* (2013.01); *A61B 1/0005* (2013.01);
(Continued)

(58) Field of Classification Search
CPC ....... A61B 5/006; A61B 6/032; A61B 1/2676; A61B 1/0005; A61B 1/00009; A61B 10/02
See application file for complete search history.

(56) References Cited

U.S. PATENT DOCUMENTS 5,891,030 A    4/1999    Johnson et al.
5,971,767 A    10/1999    Kaufman et al.
(Continued)

FOREIGN PATENT DOCUMENTS

JP    2001511031 A    8/2001
JP    2005304937 A    11/2005
JP    2006020874 A    1/2006

OTHER PUBLICATIONS

J.D. Gibbs et al., "3D MDCT-Based System for Planning Peripheral Bronchoscopic Procedures", Computers in Biology and medicine, new York, NY, US, vol. 39, No. 3, Mar. 1, 2009, pp. 266-279.

(Continued)

*Primary Examiner* — Bo Joseph Peng

(57) ABSTRACT

A method, system, and program product are provided for user-steered, on-the fly path planning in an image-guided endoscopic procedure, comprising: presenting, on a display, a 2D sectional image showing a region of interest from a preoperative CT scan; defining a control point on the 2D sectional image within a patient's body lumen responsive to a first user input; centering the control point; adjusting a viewing angle about the control point to show a longitudinal section of the body lumen responsive to a second user input; identifying a second point on a planned path within the body lumen responsive to a third user input; extending a planned path connecting the control point and the second point; redefining the second point as a new control point; and repeating the presenting adjusting, identifying, extending, and the redefining steps until the planned path reaches a procedure starting point within the patient's body.

15 Claims, 7 Drawing Sheets

(51) Int. Cl.
  *A61B 1/267* (2006.01)
  *A61B 6/03* (2006.01)
  *A61B 10/02* (2006.01)

(52) U.S. Cl.
  CPC ........ *A61B 1/00009* (2013.01); *A61B 1/2676* (2013.01); *A61B 6/032* (2013.01); *A61B 10/02* (2013.01)

(56) References Cited

U.S. PATENT DOCUMENTS

| | | | |
|---|---|---|---|
| 6,928,314 B1* | 8/2005 | Johnson | G06T 7/606 128/920 |
| 9,037,215 B2 | 5/2015 | Higgins et al. | |
| 2005/0107679 A1 | 5/2005 | Geiger et al. | |
| 2005/0182295 A1* | 8/2005 | Soper | A61B 1/0008 600/117 |
| 2005/0261550 A1* | 11/2005 | Akimoto | A61B 1/00009 600/117 |
| 2006/0072799 A1* | 4/2006 | McLain | G06T 5/009 382/128 |
| 2006/0084860 A1 | 4/2006 | Geiger et al. | |
| 2007/0024617 A1* | 2/2007 | Poole | G06T 7/0083 345/424 |
| 2007/0127792 A1* | 6/2007 | Virtue | A61B 6/032 382/128 |

OTHER PUBLICATIONS

D. Lesage et al., "A Review of 3D Vessel Lumen Segmentation Techniques: Models, Features and Extraction Schemes", Medical Image Analysis, Oxford University Press, Oxford, GB, vol. 13, No. 6, Dec. 1, 2009, pp. 819-845.

A. Gulsun et al., "Robust Vessel Tree modeling"., Medical Image Computing and Computer-Assisted Intervention A MICCAI, 2008, Springer Berlin, Germany, Sep. 6, 2008, pp. 602-611.

P. Taeprasartsit et al., "System for Definition of the Central-Chest Vasculare", Medical Imaging 2009: Image Processing Josien P.W. Pluim, et al., Dawantlake Buena Vista, FL, Conference vol. 7259, vol. 7259, Feb. 7, 2009, pp. 1-15.

D. Mueller et al., "Robust Semi-Automated Path Extraction for Visualising Stenosis of the Coronary Arteries"., Computerized medical Imaging and Graphics, Pergamon Press, New York NY US, Sep. 1, 2008, vol. 32, No. 6, pp. 463-475.

K. Poon et al., "Live-Vessel: Extending Livewire for Simultaneous Extraction of Optimal Medial and boundary Paths in Vascular Images"., Medical Image Computing and Computer-Assisted intervention A MICCAI 2007, Oct. 29, 2007, Springer Berlin, Germany, pp. 444-451.

A.M. Kanitsar, "Advanced Visualization Techniques for Vessel investigation, Chapter 5; Vessel Investigation", Dissertation Tu Wien, Feb. 13, 2001, pp. 37-52.

T. Deschamps et al., "Automatic Construction of minimal Paths in 3D Images: An Application to Virtual Endoscopy", Cars, Computer Assisted Radiology and surgery, Proceedings of the International Congress and Exhibition, Proceedings of the international Symposium on Computer Assisted Radiology and Surgery, Jun. 23, 1999, pp. 151-155.

S. Olabarriaga et al., "Interaction in the Segmentation of medical Images: A Survey", Medical Image Analysis, Oxford University Press, Oxford, GB, Jun. 13, 2001, vol. 5, No. 2, pp. 127-142.

K. Lu and W. E. Higgins, Interactive segmentation based on the live wire for 3D CT chest image analysis, International Journal of Computer Assisted Radiology and Surgery, vol. 2, No. 3-4, pp. 151-167, Dec. 2007.

W. E. Higgins, J. P. Helferty, K. Lu, S. A.Merritt, L. Rai, and K.-C. Yu, 3D CT-video fusion for image-guided bronchoscopy, Computerized Medical Imaging and Graphics, vol. 32, No. 3, pp. 159-173 Apr. 2008.

* cited by examiner

USER-STEERED ON-THE-FLY PATH PLANNING

CROSS-REFERENCE TO PRIOR APPLICATIONS

This application is the U.S. National Phase application under 35 U.S.C. § 371 of International Application Serial No. PCT/IB2012/052241, filed on May 4, 2012, which claims the benefit of U.S. Application Ser. No. 61/484,479, filed on May 10, 2011. These applications are hereby incorporated by reference herein.

FIELD OF THE INVENTION

The invention relates to the field of image-guided medical intervention and more particularly to a method and system for user-steered, on-the-fly path planning for a intervention procedure.

BACKGROUND

Lung cancer has remained the leading cause of cancer death in the United States and worldwide for many years. The standard diagnostic approach for lung cancer involves a full chest pre-operative computerized tomography (CT) scan followed by sampling of suspected regions of interest (ROIs) through either bronchoscopy or percutaneous needle biopsy. Bronchoscopy is often preferred because it is a minimally invasive procedure with a fast patient recovery period, and it has been recognized as a safe and effective approach for lung cancer diagnosis and staging.

After the CT scan and prior to sampling ROIs using a bronchoscope, a preliminary but critical step is to find a feasible path (way) for the bronchoscope to travel through the patient's bronchial tree and reach a location close enough to the ROIs to perform biopsies. Traditionally, a physician first studies the diagnostic CT scan to detect suspected ROIs. For each ROI, he/she then starts at a location close to the ROI and traces visible cues of the patient's bronchial tree on 2D sectional images, usually axial slices. The cues are pieces of bronchi on 2D images, appearing as elliptical dark regions surrounded by lighter areas (soft-tissue bronchial walls).

Using these visible cues, the physician can reconstruct a feasible path to allow a bronchoscope to travel through the patient's bronchial tree, reach a location close enough to the suspect ROI, and perform a suitable biopsy procedure. However, the physician must reconstruct the paths mentally and memorize each path for individual ROIs before the procedure. As a result, path planning, without computer-aided assistance, can be burdensome for the physician, and it requires rich skills and experience.

With the development of CT and interventional guidance techniques, considerable efforts have been undertaken to develop image-based or electromagnetic-based navigation systems for planning and guiding bronchoscopic procedures (e.g., Broncus LungPoint® Virtual Bronchoscope Navigation System, Superdimension i-logic System™). In these approaches, path planning is integrated into the systems as a vital step prior to real-time guidance of surgical procedures and driven to provide an optimal path or path candidates nearly automatically to reach individual ROIs.

These existing automated approaches require a high-resolution CT scan prior to the bronchoscopic procedure. A powerful segmentation method to extract a full human bronchial tree structure from the CT images, and an intelligent optimum path search process. These requirements are not trivial. A full segmentation of a human bronchial tree structure from a CT scan is difficult and time-consuming. This is especially true when small airway bronchi are involved when dealing with peripheral ROIs. The segmentation requires considerable processing time, and may still require human interaction. Moreover, the segmentation results are highly dependent upon the quality of the pre-operative CT images. Due to the high processing time, these automated approaches are not practical when the patient is on the table.

Even with good bronchial tree segmentation, the optimal path planning approach must also take account for parameters of the endoscope that will be used to reach each ROI in order to generate feasible paths. The parameters of the endoscope, however, may not be available at the time that path planning is performed, and the physician may change endoscopes during the procedure.

Automated path planning approaches will usually result in multiple path candidates, and the physician will have to study each candidate and chose a feasible path from among the candidates. Some times none of the candidates will be a feasible path, and the physician will need to rely on his/her experience, instead of following the chosen path. Also, the generation of multiple path candidates represents a significant processing burden.

Thus, the automated path planning approaches: (1) may not be available when there is not sufficient data (e.g., high resolution CT and endoscope parameters); (2) are not feasible for on-the-table diagnosis and planning, which is preferred in most real clinical applications; (3) may not be necessary because a bronchoscopic procedure is often performed to deal with one to three ROIs, and the physician may prefer to rely on the bronchial cues plan a path for the procedure; and (4) may provide multiple or unreliable paths.

SUMMARY

The present invention provides a method, system and program product for assisting in image-guided endoscopic intervention. Embodiments of the present invention allow a physician to perform user-steered, on-the-fly path planning without the need for high resolution CT images or airway-tree segmentation. As a result, the path can be planned when the patient is on the scanner table.

According to one embodiment a method is provided for user-steered, on-the fly path planning in an image-guided endoscopic procedure, comprising: presenting, on a display, a 2D sectional image showing a region of interest from a preoperative CT scan; defining a control point on the 2D sectional image within a patient's body lumen responsive to a first user input; centering the control point; adjusting a viewing angle about the control point to show a longitudinal section of the body lumen responsive to a second user input; identifying a second point on a planned path within the body lumen responsive to a third user input; extending a planned path connecting the control point and the second point; redefining the second point as a new control point; and repeating the presenting, adjusting, identifying, extending, and the redefining steps until the planned path reaches a procedure starting point within the patient's body. The body lumen traversed is advantageously in a tree-shaped anatomic structure such as a lung or vasculature.

According to one embodiment the control point and the second point are voxels on the displayed image and the step of creating a planned path comprises repeatedly performing a cost analysis to link a neighboring voxel to a last voxel on the planned path starting at the control point. According to one embodiment the step of extending a planned path comprises using a graphic search application based on gradient relevant features and an optimal path searching method.

According to one embodiment the cost analysis analyzes intensity attributes for each neighboring voxel to select a voxel to link on the planned path and a weight factor for each attribute. In one embodiment the cost analysis further analyzes geometric characteristics for each neighboring voxel select a voxel to link on the planned path.

In one embodiment the endoscope is a bronchoscope, the procedure is a biopsy of lung tissue, and the control point is initially set in a branch of the patient's bronchial tree near a suspected tumor identified in a sectional image of a multi-planar reconstruction from a CT scan.

Optionally, the planned path may be presented on the display as a representation of the bronchoscope image with the planned path marked thereon as a contrasting thread.

According to one embodiment the endoscope is a bronchoscope, the procedure is a biopsy of lung tissue, the control point is initially set in a branch of the patient's bronchial tree near a suspected tumor identified in a sectional image of a multi-planar reconstruction from a CT scan, and the patient's bronchial tree is presented on the display as a three-dimensional image with the path segments indicated thereon.

In one embodiment the created path segment is presented on the display for approval, and in response to not receiving an approval, the method further comprises generating a new candidate path segment from the control point to the second point.

According to one embodiment the cost analysis uses gradient relevant attributes for each neighboring voxel to select a voxel to link on the planned path and the new candidate path segment is created using the cost analysis with at least one change to one of the attributes or weight factors.

According to one embodiment a system is provided for user-steered, on-the fly path planning in an image-guided bronchoscopic procedure. The system comprises a processor, a memory operably connected to the processor, a display operably connected to the processor; and a program of instructions encoded on the memory and executable by the processor. When the program of instructions is executed by the processor, it presents, on a display, a 2D sectional image showing a region of interest from a preoperative CT scan. The program of instructions also defines a control point on the 2D sectional image within a branch of a patient's bronchial tree responsive to a first user input, and presents a new image centered at the control point. The program of instructions adjusts a viewing angle about the control point to show a longitudinal section of the branch responsive to a second user input. The program of instructions identifies a second point on a planned path within the branch responsive to a third user input. Then, the program of instructions extends a planned path connecting the control point and the second point, and redefines the second point as a new control point. The program of instruction repeats the presenting step, the adjusting step, the identifying step, the extending step, and the redefining step until the planned path reaches the trachea.

According to one embodiment a computer program product is provided comprising a computer-readable storage medium having encoded thereon program code for user-steered, on-the fly path planning in an image-guided endoscopic procedure, comprising: program code for presenting, on a display, a 2D sectional image showing a region of interest from a preoperative CT scan; program code for defining a control point on the 2D sectional image within a patient's body lumen responsive to a first user input; program code for presenting a new image centered at the control point; program code for adjusting a viewing angle about the control point to show a longitudinal section of the body lumen responsive to a second user input; program code for identifying a second point on a planned path within the body lumen responsive to a third user input; program code for extending a planned path connecting the control point and the second point; program code for redefining the second point as a new control point; and program code for repeating the presenting step, the adjusting step, the identifying step, the extending step, and the redefining step until the planned path reaches a procedure starting point within the patient's body.

According to one embodiment, the cost analysis program instructions further comprise instructions for analyzing geometric characteristics for each neighboring voxel select a voxel to link on the planned path. According to one embodiment, the program instructions for extending a planned path comprise instructions for using a graphic search application based on gradient relevant features and an optimal path searching function.

According to one embodiment, the endoscope is a bronchoscope, the procedure is a biopsy of lung tissue, and the program instructions for setting the control point comprise program instructions for initially setting the control point in a branch of the patient's bronchial tree near a suspected tumor identified in a sectional image of a multi-planar reconstruction from a CT scan. According to one embodiment, the program of instruction further comprises program instructions for presenting the planned path on the display as a representation of the endoscope image with the planned path marked thereon as a contrasting thread.

According to one embodiment, the endoscope is a bronchoscope, the procedure is a biopsy of lung tissue, the control point is initially set in a branch of the patient's bronchial tree near a suspected tumor identified in a sectional image of a multi-planar reconstruction from a CT scan, and the program of instructions further comprises program instructions for presenting the patient's bronchial tree on the display as a three-dimensional image with the path segments indicated thereon.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

The present invention provides a method, system and program product for user-steered, on-the fly path planning in an image-guided endoscopic procedure. According to one embodiment, the endoscope is a bronchoscope used for performing a biopsy. Starting at a location that is close to an ROI and inside a bronchus, a user defines a suitable path on images generated from a CT scan. With several mouse clicks the user can steer a 2D local sectional image and interactively select dynamically calculated candidate path segments. The process follows the standard workflow in surgical planning for bronchoscopy by seeking cues of bronchial structures that lead to target ROIs. The user-friendly interface setting allows for the best presentation of an airway path in a selected 3D sub-volume by providing flexibly oriented 2D sectional views, instead of traditional transverse (or axial), coronal, and sagittal views. The user can easily study or review the case and define a suitable path at the same time.

Figure 1:
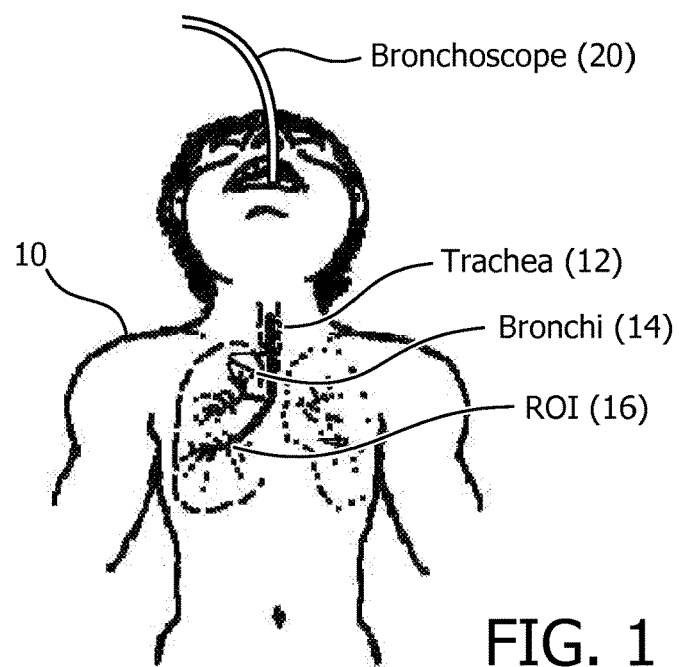
FIG. 1 is an isometric view of a patient undergoing a bronchoscopic procedure with a section view showing the patients trachea, bronchi, and cancer.
Figure 2:
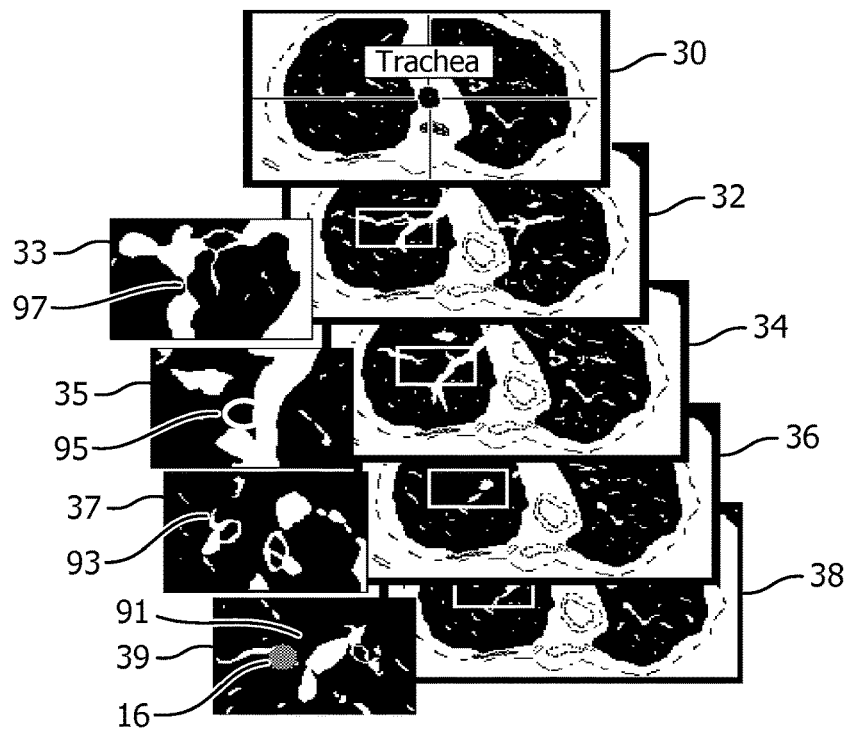
FIG. 2 is a multi-planar reconstruction (MPR) from a CT scan showing a cancer and bronchial cues usable for path planning.

FIG. 1 shows a patient 10 undergoing a broncoscopic procedure. A physician guides a bronchoscope 20 through the patient's trachea 12 and into a bronchi 14 proximate a region of interest (ROI) 16. Then a biopsy is performed through the bronchial wall at the ROI 16. A pre-operative CT scan is performed for use in guiding the bronchoscope 20 through the bronchi 14 to the ROI 16. As shown in FIG. 2, for a bronchoscopic procedure, the CT scan is presented as progressive axial sectional views 30, 32, 34, 36, 38 of the patient's chest. FIG. 2 shows portions of sectional views 32, 34, 36, and 38 expanded to provide expanded views 33, 35, 37, and 39, respectively. An image of an ROI 16 is identified on the expanded view 39.

In the traditional planning approach, a physician identifies a first cue 91 near the ROI 14 on expanded sectional view 39. In the illustrated embodiment the first cue 91 is a broncus 14 having an axis intersecting the plane of the image. Then, the physician identifies cues 93, 95, 97 in each successive expanded view 37, 35, 33 to define a path for the brochoscopic intervention leading from the tracea to the ROI 14. The physician relies on his knowledge of the bronchial tree to connect the cues, and mentally constructs and memorizes a path to each ROI.

In an embodiment of the present invention, the physician identifies the first cue 91 on a display and defines it as a first control point through a user interface. The system centers the control point on the display. The physician adjusts the viewing angle around the control point. Then the physician identifies a second point on the planned path. The system generates a path segment in a patients airway connecting the control point and the second point. The system defines the second point as a new control point and centers it on the display. A path segment can then be added to the planned path by identifying a third point on the planned path. New segments are added until the planned path reaches a start point for the procedure, such as the patient's trachea.

Figure 3:
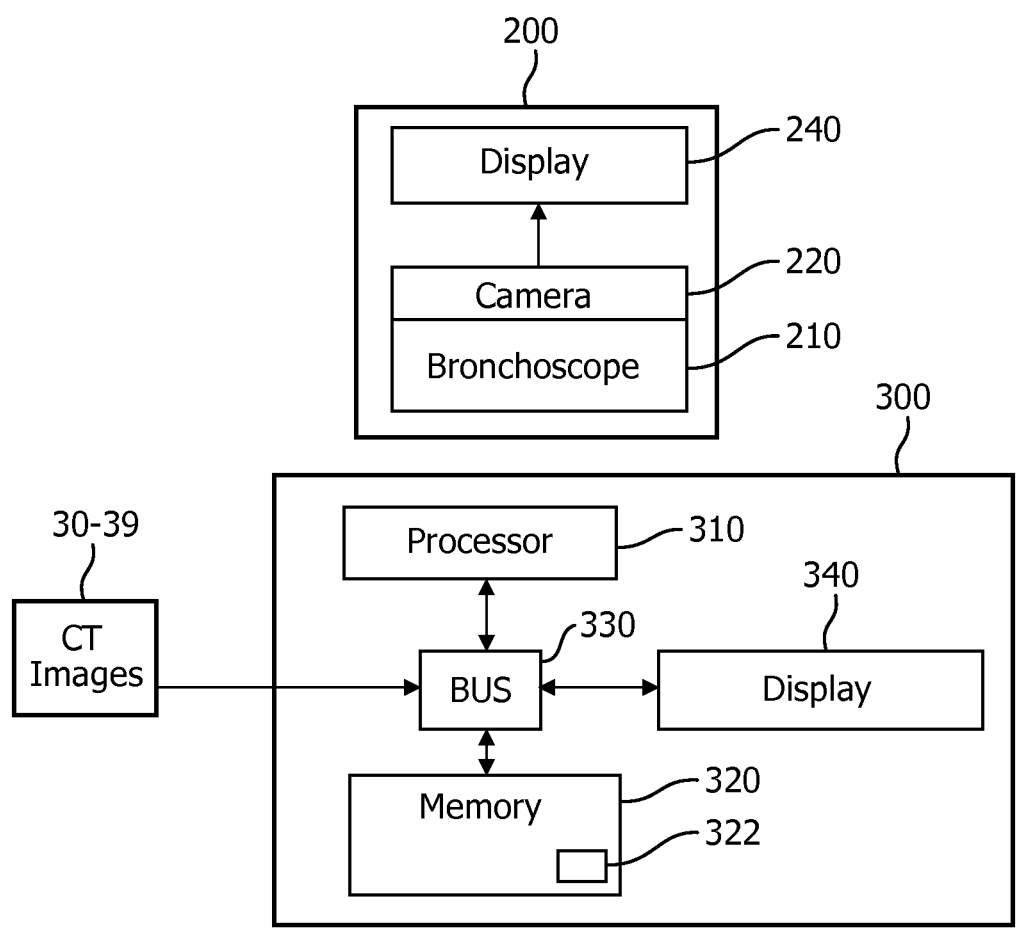
FIG. 3 is a block diagram of a system for user-steered, on-the fly path planning in an image-guided bronchoscopic procedure, according to an embodiment of the present invention.

FIG. 3 is a block diagram of a system for user-steered, on-the-fly plath planning for an endoscopic intervention according to an embodiment of the present invention. A processing unit 300 comprises a processor 310 which is operably connected to a memory 320. According to one embodiment, they are connected through a bus 330. The processor 310 may be may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like.

A display 340 is also operably connected to the processor 310. The display may be any monitor, screen, or the like suitable for presenting a graphical user interface (GUI) capable of presenting medical images.

The system also comprises a means for importing a CT scan into the processor 310. This means may be a network connection for importing the CT scan over the Internet or an intranet. Alternatively, the means may be a storage drive, such as a CD-drive, a USB port suitable for inserting a flash drive. In yet another embodiment, the means may be a direct wired or wireless connection to a C-arm that performs the CT scan.

In the illustrated embodiment, the endoscope is a bronchoscope system 200. The bronchoscope system 200 comprises a bronchoscope 210 fitted with a camera 220 to provide visualization of the inside of the bronchial airways during the intervention. The camera 220 is operably connected to a display 240 which presents the bronchial image to the physician.

The memory 320 has encoded thereon a program of instruction executable by the processor 310. When the program of instruction 322 is executed by the processor 310, it provides a user-steered, on-the-fly planning method for an intervention endoscopic procedure, an example of which is described below.

Figure 4:
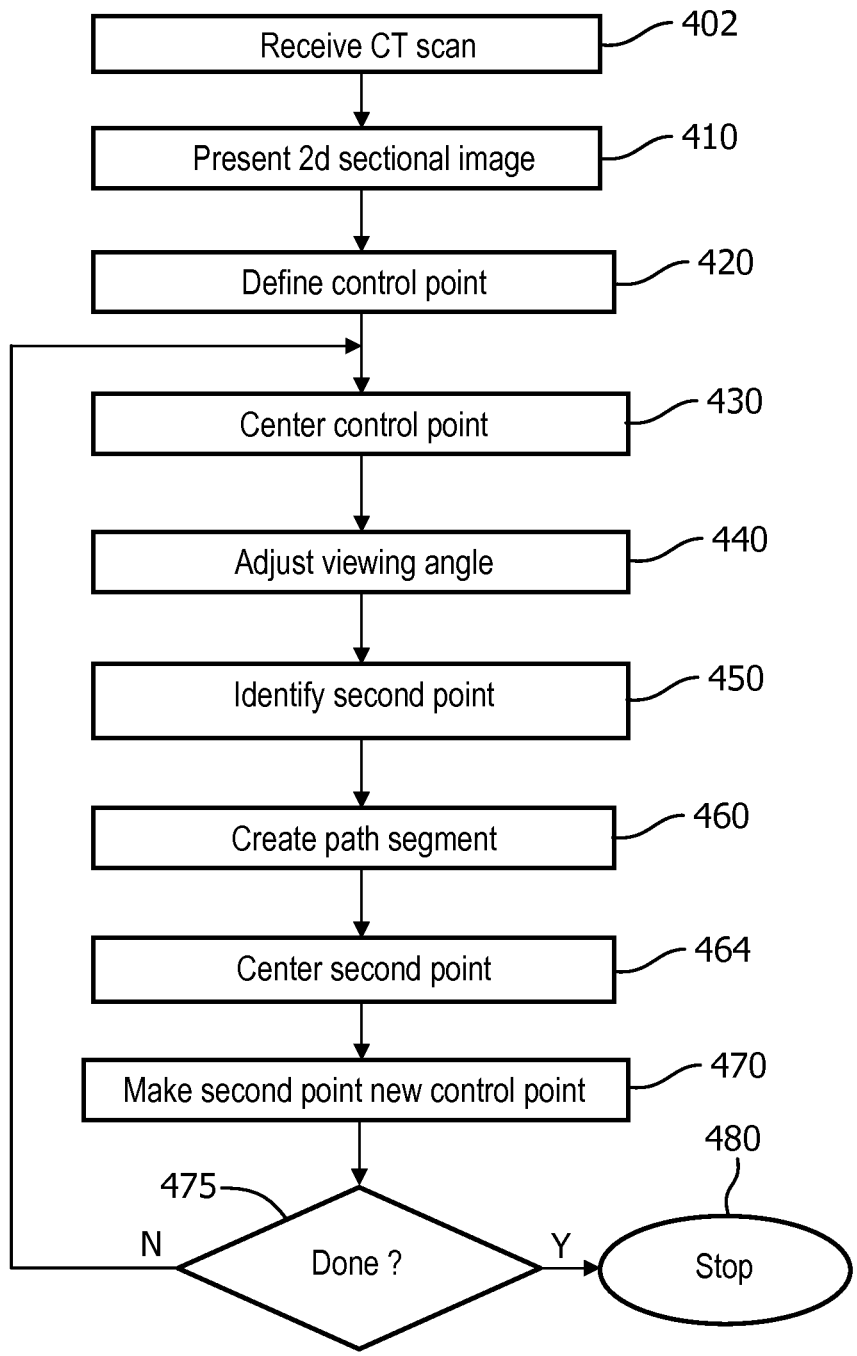
FIG. 4 is a flow diagram of a method for user-steered, on-the-fly planning of an intervention procedure, according to an embodiment of the present invention.

FIG. 4 is a flow diagram of a method for user-steered, on-the-fly planning for an endoscopic procedure. In this example, the procedure is a biopsy using a bronchoscope.

The program of instruction 322 receives a pre-operative CT scan (Step 402). The CT scan may be in the form of a 3D image space, from which a series of sectional images such as 30 and 32-39 shown in FIG. 2 can be generated.

Figure 6A:
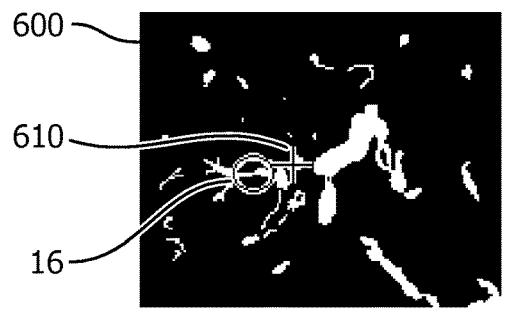
FIGS. 6A-C, 7A-C, and 8A-C show sequential steps of a method for forming path segments, according to an embodiment of the present invention.

The program of instruction 322 presents a sectional image (600 in FIG. 6A) on the display 430 showing a ROI 16 (Step 410). The sectional image 600 may be selected from a plurality of sectional images, such as images and 32 shown in FIG. 2. In the illustrated example, the sectional image 600 is an axial sectional image.

The physician selects a control point on the displayed image 600 that is within a broncus 14 near the ROI 16, similar to identifying a cue 91 in the traditional planning method. The physician may, for example, move a crosshair to the first cue 91 by manipulating a mouse, then select the first cue 91 as the first control point with a mouse click.

In response the physician's selection action for the control point, the program of instruction 322 defines a control point 610 at the indicated location on the sectional image 600 (Step 420). Control point 610 is a voxel in the sectional image which corresponds to a point in three-dimensional space located on the plane of the sectional images 600.

The program of instruction presents a new image centered at the control point 610 (Step 430). That is, the field of view is translated to center the control point 610 on the display 340.

Figure 6B:
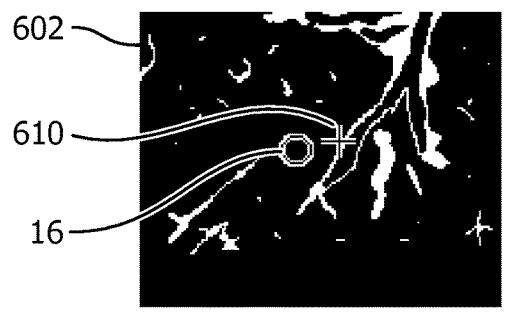

In response to a user input, the program of instruction 322 adjusts a viewing angle about the control point 610 to present a new image 602 which shows a longitudinal section of the body lumen (bronchus) (Step 440), as shown in FIG. 6B. The physician may use arrow keys on a keypad (not shown) or mouse cursor (not shown) operably connected to the processor 310 to rotate the field of view left-right and up-down, about the fixed control point 610, for example. Responsive to this input, the processor 310 may calculate and present at the display 340 an image 602 corresponding to a section of the 3D image space at the new viewing angle. At this angle, the bronchial airway appears as a dark channel 14A between two lighter regions (the bronchial walls) 14B.

Figure 6C:

The physician identifies a second point in the bronchial airway 14, as shown in FIG. 6C. The physician may, for example, move a crosshair to the a point in the airway near the edge of the field of view on the display by manipulating a mouse, then select the point at the crosshair as the second point 620 with a mouse click.

Responsive to this third input, the program of instruction defines the second point 620 on the indicated voxel, where the crosshair is located, on a planned path within the bronchus (step 450).

With the control point 610 and the second point 620 on the planned path defined, the program of instruction creates a path segment 630 connecting the control point 610 and the second point 620 (Step 460). The path segment 630 is created within the airway 14A using a cost analysis, as will be described in greater detail below.

Figure 7A:

Once the path segment 630 is created, the second point 620 is centered in the field of view of the display (Step 464) as shown in FIG. 7A, and the second point 620 is redefined as a new control point 610A (Step 470). If the new control point 610A is at a beginning point for the planned path, such as the patient's trachea, the physician can provide an input to indicate the path is complete, and the program of instruction stops (step 480).

The program of instruction may test for completion (Step 475) by monitoring for the user input, or may time out if an input is not received for a predefined period of time, or may use any other suitable test for completion.

Figure 7B:
Figure 7C:
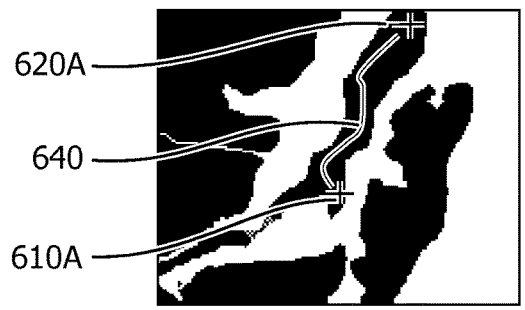
Figure 8A:
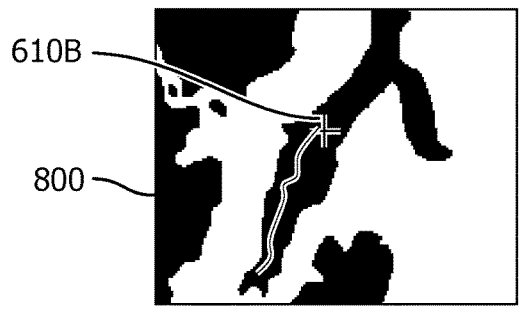
Figure 8B:

If the path is not completed, then the program of instruction 322 repeats the steps for adjusting the viewing angle (Step 440) to provide a cross section 702 showing the airway 14A as shown in FIG. 7B, identifying a new second point 620A (Step 450) as shown in FIG. 7C, creating a new path segment 640 (step 460) as shown in FIG. 7C, centering the new second point 620A to provide a new image 800 as shown in FIG. 8A, and redefining the new second point 620A as third control point 610B (Step 470), until the path is completed.

Figure 8C:

As shown in FIG. 8C, if the path is not completed at the third control point 610B, the viewing angle is adjusted again to provide a cross section 802 showing the airway 14A (Step 440). Then, a third second point 620B is defined (step 450) and a third path segment 650 is generated connecting the third control point 610B to the third second point 620B (step 460).

Figure 6D:
FIGS. 6D, 7D, and 8D show respective path segments on a 3D image of a patient's bronchial tree, according to an embodiment of the present invention.
Figure 7D:
Figure 8D:
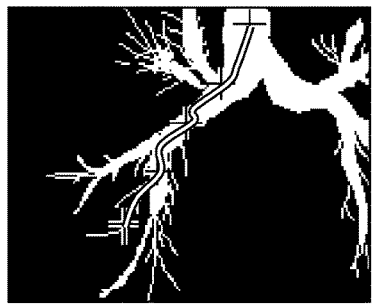

Optionally, the program of instruction 322 Figs. may present the patient's bronchial tree as three-dimensional representation on the display 340 with the path segments 630, 640, 650 indicated on the bronchial tree as shown in FIGS. 6D, 7D, and 8D.

Figure 5:
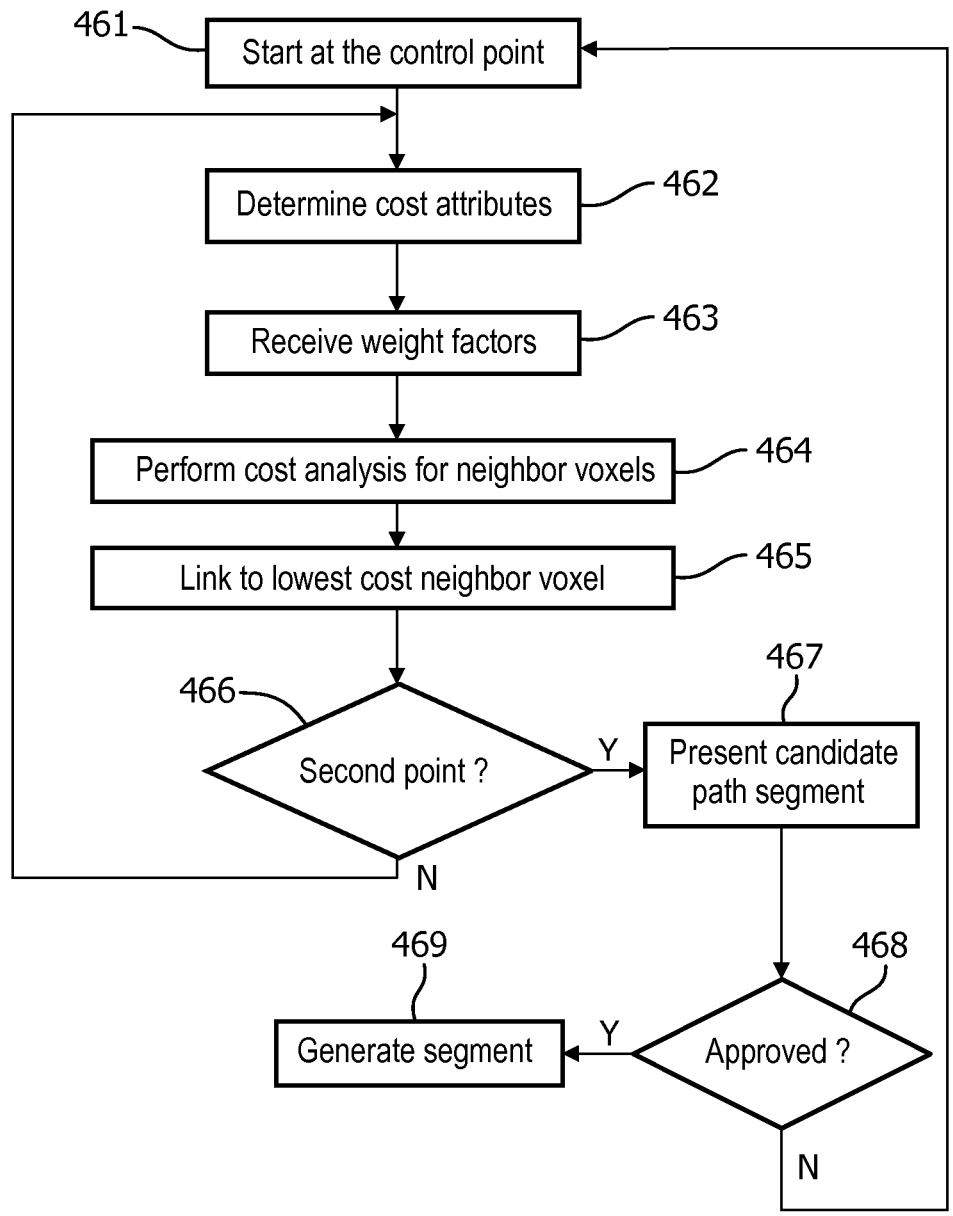
FIG. 5 is a flow diagram of a method for extending a planned path connecting the control point and the second point, according to an embodiment of the present invention.

FIG. 5 is a flow diagram of a method for extending a planned path connecting the control point and the second point, according to an embodiment of the present invention. The program of instruction 322 comprises program instructions for dynamically searching for a path candidate between two points defined on the planned path. The program instructions reduce a boundary problem (finding a path inside of the airway walls) to a graphic search using a cost function based on gradient relevant features.

The two dimensional images 600, 602, 700, 702, 800, 802 are each comprised of a single layer of voxels (picture elements representing a points in three-dimensional space). Voxels on the planned path are defined as path elements P, and each path element P is built on previous path elements to form a path segment 630, 640, 650, using the control point 610 as a starting point. Thee new path element P is determined by comparing the local cost l for each of the eight neighboring voxels r. A path element P and it's eight neighboring voxels r form a neighborhood N. Each neighboring voxel r is a candidate path element.

The control point 610, 610A, 610B is defined as the first path element (step 461). The program of instruction 322 determines cost attributes for neighboring voxels r (Step 462). The cost attributes are gradient relevant features of the voxels in an image. According to various embodiments of the invention, cost attributes include functions of one or more of: light intensity for a neighboring voxel $f_I(r)$, the mean value of light intensity for a neighborhood of a neighboring voxel $f\mu(r)$, the standard deviation of light intensity for a neighborhood of a neighboring voxel $f\delta(r)$, the radius of a minimum circle that centers at a neighboring voxel and intersects the bronchial wall $f_R(r)$.

Additionally, cost attributes may include functions of similarity between a path element P and a neighboring proposed path element r. For example, cost elements may include a function of similarity of intensity $f_{II}(p,r)$ and a function of similarity of the radius of a minimum circle that centers at the path element P to the radius of a minimum circle that centers at the proposed path element r $f_{RR}(p,r)$, where:

$$f_{II}(p,r)=|Ip-Ir| \quad (1)$$

$$f_{RR}(p,r)=|Rp-Rr| \quad (2)$$

The cost attributes may further include a function of a feature that reduces the likelihood of the planned path from doubling back on itself $f_D(r)$. In this function, $f_D$, the previous path element voxel would have a higher value than the other neighboring voxel.

The cost attributes may be measured and/or calculated, depending upon the particular attribute, for each voxel neighboring the previous path element P.

The program of instruction receives user supplied weight factors $w_1$, $w_\mu$, $w_\delta$, $w_R$, $W_{II}$, $W_{RR}$, $W_D$ for each respective cost attribute (Step 463). The physician may select weighting factors at the time of path planning, or the factors may be stored in sets based optimized for particular applications and selected as a set identified with an intended application. The applications may be particular parts of the bronchial tree where the ROI 14 is located, the style of bronchoscope, other relevant application details, or combinations thereof. Moreover, the sets of weight factors may be optimized values derived for the specific application.

The program of instructions 322 performs a cost analysis for each neighboring voxel r of the most recent path element P to calculate a local cost L(p,r) for linking r to P (Step 464), where:

$$L(P,r)=w_I f_I(r)+w_\mu f_\mu(r)+w_\delta f_\delta(r)+w_R f_R(r)+W_{II} f_{II}(P,r)+W_{RR} f_{RR}(P,r)+W_D f_D(P,r) \quad (3)$$

The neighboring voxel r with the lowest cost value is defined as the next path element $P_{next}$, and linked to the previous path element P to extend the path segment 630, 640, 650 (Step 465).

The next path element $P_{next}$ is compared to the second point 620, 620A, 620B to determine whether or not the path segment 630, 640, 640 has reached the second point 620, 620A, 620B (step 466).

If the next path element $P_{next}$ is not the second point 620, 620A, 620B (N branch at Step 466), then the program of instruction 322 determines cost attributes for the neighboring voxels r of the next path element Pnext (Step 462), receives weighting factors (Step 463), performs a new cost analysis for the voxels neighboring the next path element $P_{next}$ (Step 464), defines the lowest cost neighboring element r as the next path element $P_{next2}$, and compares this next path element $P_{next2}$ the second point 620, 620A, 620B to determine whether or not the path segment 630, 640, has reached the second point 620, 620A, 620B (step 466). This loop (Steps 462-466) is repeated until a next path segment is the second point (Y branch at Step 466).

If the path segment 630, 640, 650 has reached the second point 620, 620A, 620B (Y branch at Step 466), then the program of instruction 322 presents the newly generated path segment connecting the control point 610, 610A, 610B and the second point 620, 620A, 620B as a candidate path segment on a 2D image 6C, 7C, 8C on the display 340 (Step 467).

The physician may approve the candidate path segment or disapprove it. The physician may enter his/her approval/disapproval by a mouse click, or any other suitable input means. The program of instruction 322 determines whether or not it has received an approval (Step 468). If the program of instruction 322 receives an approval (Y branch at Step 468), then the program of instruction 322 generates the path segment (step 469) and centers the second point in the field of view of the display 430 (Step 464 in FIG. 4).

If the candidate path segment is not approved (N branch at Step 468), then the program of instruction 322 again starts at the control point 610, 610A, 610B (Step 461) and generates a new candidate path segment using cost analysis (Steps 462-469). In the new cost analysis, the weight factors may be changed by either the physician or the program of instruction, and the cost attributes may be changed by adding and/or deleting cost attributes.

The invention can take the form of program instructions encoded on a tangible medium. As such, the invention can be an entirely hardware embodiment, an entirely software embodiment or an embodiment containing both hardware and software elements. In an exemplary embodiment, the invention is implemented in software, which includes but is not limited to firmware, resident software, microcode, etc.

Furthermore, the invention may take the form of a non-volatile computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A method for user-steered, on-the fly path planning in an image-guided endoscopic procedure, comprising:
   presenting, on a display, a 2D image showing a cross-sectional field of view of a region of interest from a preoperative CT scan;
   defining a control point on the 2D image corresponding to a location within a patient's body lumen responsive to a first user input, wherein the body lumen has an axis that intersects a plane of the 2D image;
   presenting a new 2D image centered at the control point;
   adjusting a viewing angle by rotating the field of view about the control point to display another new 2D image showing a cross-sectional view of the body lumen responsive to a second user input wherein the view of the body lumen has an axis that does not intersect a plane of the another 2D image such that the view of the body lumen appears as a dark channel between two lighter regions;
   identifying a second point on a planned path on the another new 2D image corresponding to a location within the body lumen responsive to a third user input;
   extending a planned path connecting the control point and the second point;
   redefining the second point as a new control point; and
   repeating the presenting step, the adjusting step, the identifying step, the extending step, and the redefining step until the planned path reaches a procedure starting point within the patient's body.

2. The method of claim 1, wherein the control point and the second point are voxels on the displayed image and the step of creating a planned path comprises repeatedly performing a cost analysis to link a neighboring voxel to a last voxel on the planned path starting at the control point.

3. The method of claim 2, wherein the cost analysis analyzes intensity attributes for each neighboring voxel to select a voxel to link on the planned path and a weight factor for each attribute.

4. The method of claim 3, wherein the cost analysis further analyzes geometric characteristics for each neighboring voxel select a voxel to link on the planned path.

5. The method of claim 2, the path segment wherein the created path segment is presented on the display for approval, and in response to not receiving an approval, the method further comprises generating a new candidate path segment from the control point to the second point.

6. The method of claim 5, wherein the cost analysis uses gradient relevant attributes for each neighboring voxel to select a voxel to link on the planned path and the new candidate path segment is created using the cost analysis with at least one change to one of the attributes or weight factors.

7. The method of claim 1 wherein the step of extending a planned path comprises using a graphic search application based on gradient relevant features and an optimal path searching function.

8. The method of claim 7, wherein the planned path is presented on the display as a representation of the bronchoscope image with the planned path marked thereon as a contrasting thread.

9. The method of claim 7, wherein the endoscope is a bronchoscope, the procedure is a biopsy of lung tissue, the control point is initially set in a branch of the patient's bronchial tree near a suspected tumor identified in a image of a multi-planar reconstruction from a CT scan, and the patient's bronchial tree is presented on the display as a three-dimensional image with the path segments indicated thereon.

10. The method of claim 1, wherein the intervention procedure is performed in a tree-shaped anatomic structure and the path is planned through the tree-shaped anatomic structure.

11. The method of claim 10, wherein the endoscope is a bronchoscope, the procedure is a biopsy of lung tissue, the tree-shaped anatomic structure comprises a patient's bronchial tree, and the control point is initially set in a branch of the patient's bronchial tree near a suspected tumor identified in a image of a multi-planar reconstruction from a CT scan.

12. The method of claim 10, wherein the tree-shaped anatomic structure comprises a patient's blood vessels.

13. A system for user-steered, on-the fly path planning in an image-guided bronchoscopic procedure, comprising:
   a processor;
   a memory operably connected to the processor;
   a display operably connected to the processor; and
   a program of instructions encoded on the memory and executable by the processor to:
      present, on a display, a 2D image showing a cross-sectional field of view of a region of interest from a preoperative CT scan;
      define a control point on the 2D image corresponding to a location within a branch of a patient's bronchial tree responsive to a first user input, wherein the branch of the bronchial tree has an axis that intersects a plane of the 2D image;
      present a new 2D image centered at the control point;
      adjust a viewing angle by rotating the field of view about the control point to display another new 2D image showing a cross-sectional view of the branch responsive to a second user input wherein the view of the branch has an axis that does not intersect a plane of the another 2D image such that the view of the branch appears as a dark channel between two lighter regions;
      identify a second point on a planned path on the another new 2D image corresponding to a location within the branch responsive to a third user input;
      extend a planned path connecting the control point and the second point;
      redefine the second point as a new control point; and
      repeat the presenting step, the adjusting step, the identifying step, the extending step, and the redefining step until the planned path reaches the trachea.

14. A computer program product comprising a non-transitory, computer-readable storage medium having encoded thereon program code for user-steered, on-the fly path planning in an image-guided endoscopic procedure, comprising:
   program code for presenting, on a display, a 2D image showing a cross-sectional field of view of a region of interest from a preoperative CT scan;
   program code for defining a control point on the 2D image corresponding to a location within a patient's body lumen responsive to a first user input, wherein the body lumen has an axis that intersects a plane of the 2D image;
   program code for presenting a new 2D image centered at the control point;
   program code for adjusting a viewing angle by rotating the field of view about the control point to display another new 2D image showing a cross-sectional view of the body lumen responsive to a second user input wherein the view of the body lumen has an axis that does not intersect a plane of the another 2D image such that the view of the body lumen appears as a dark channel between two lighter regions;
   program code for identifying a second point on a planned path on the another new 2D image corresponding to a location within the body lumen responsive to a third user input;
   program code for extending a planned path connecting the control point and the second point;
   program code for redefining the second point as a new control point; and
   program code for repeating the presenting step, the adjusting step, the identifying step, the extending step, and the redefining step until the planned path reaches a procedure starting point within the patient's body.

15. The computer program product of claim 14, wherein the control point and the second point are voxels on the displayed image and the program instructions for creating a planned path comprise repeatedly performing a cost analysis to link a neighboring voxel to a last voxel on the planned path starting at the control point.

* * * * *